(12) United States Patent
Zhukov et al.

(10) Patent No.: US 8,198,019 B1
(45) Date of Patent: Jun. 12, 2012

(54) PROTEIN PROFILING FOR PREMALIGNANT TISSUE

(75) Inventors: Tatyana A. Zhukov, Lutz, FL (US); Melvyn S. Tockman, Tampa, FL (US); Roy A. Johanson, Bryn Mawr, PA (US)

(73) Assignees: University of South Florida, Tampa, FL (US); Ciphergen Biosystems, Inc., Fremont, CA (US)

( * ) Notice: Subject to any disclaimer, the term of this patent is extended or adjusted under 35 U.S.C. 154(b) by 1157 days.

(21) Appl. No.: 10/249,385

(22) Filed: Apr. 3, 2003

Related U.S. Application Data

(60) Provisional application No. 60/369,792, filed on Apr. 4, 2002.

(51) Int. Cl.
*C12Q 1/00* (2006.01)

(52) U.S. Cl. .......................................... 435/4

(58) Field of Classification Search ............... 435/7.23; 530/350; 436/174
See application file for complete search history.

(56) References Cited

U.S. PATENT DOCUMENTS 6,531,318 B1 * 3/2003 Palmer-Toy et al. ............ 436/63

OTHER PUBLICATIONS

Paweletz et al. Drug Dev. Res. 49: 34-42, 2000.*
Garvey et al. BMJ 324: 1077-1080, 2002.*
Wulfkuhle et al. Proteomics, 1: 1205-1215, 2001.*
Cazares et al. Clinical Cancer Res. 8: 2541-2552, 2002.*
Wulfkuhle et al. Nature Reviews/Cancer, 3: 267-275, 2003.*
Srinivas et al. Clinical Chemistry, 47(10): 1901-1911, 2001.*
Jacobs et al. Mol. Cel. Proteomics, 3.4: 355-366, 2004.*
Zhukov, et al. Prodeedings of the American Association for Cancer Research, Annual Meeting, (Mar. 2002), vol. 43, pp. 36. print.*
Diamandis, Clin. Chem., 2003, 49(8): 1272-1278.*
Paweletz et al.; New Technologies for Biomarker Analysis of Prostate Cancer Progression: Laser Capture Microdissection and Tissue Proteomics; Elsevier Science, Inc.; 2001.
Mass Spectrometry-based Diagnostics: The Upcoming Revolution in Disease Detection; Clinical Chemistry; 49, No. 4; 2003.
Campa et al.; Protein Expression Profiling Identifies Macrophage Migration Inhibitory Factor & Cyclophilin A as Potential Molecular Targets in Non-Small Cell Lung Cancer; DUke Unv.; Apr. 1, 2003.
Zhukov et al.; Discovery of Distinct Protein Profiles Specific for Lung Tumors & Pre-Malignant Lung Lesions by SELDI Mass Spectrometry; Elsevier Science Ireland Ltd.; 2003.

* cited by examiner

*Primary Examiner* — Hong Sang
(74) *Attorney, Agent, or Firm* — Nilay J. Choksi; Michael M. McGaw; Smith & Hopen, P.A.

(57) ABSTRACT

The present invention is a method for early detection of cancer including the steps of identifying tissue from asymptomatic individuals, gathering a substantially homogenous cell population from the tissue by laser capture microdissection (LCM), analyzing the cell population with mass spectrometry and identifying predetermined peaks in the mass spectrometry associated with an overexpression of proteins in premalignant and malignant cells.

8 Claims, 18 Drawing Sheets

Fig. 1
**Examples of Representative Sections from
Different Lung Tumors before and after Laser
Capture Microdissection**
Sq. cell carcinoma
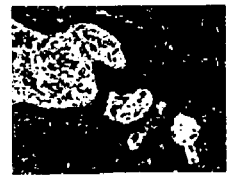
Normal bronchial cells
SqCCa after LCM
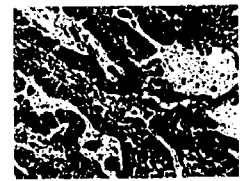
Adenocarcinoma
Normal alveolar cells
Adenocarcinoma after LCM
Adeno, BAC features
AAH adjacent to BAC

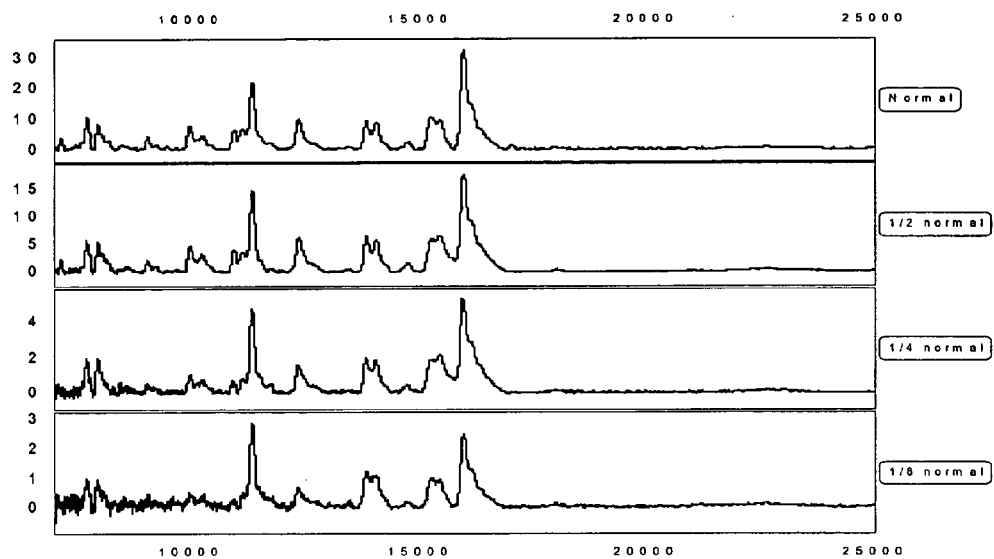
Figure 2a. Different Amounts of Normal Lysate
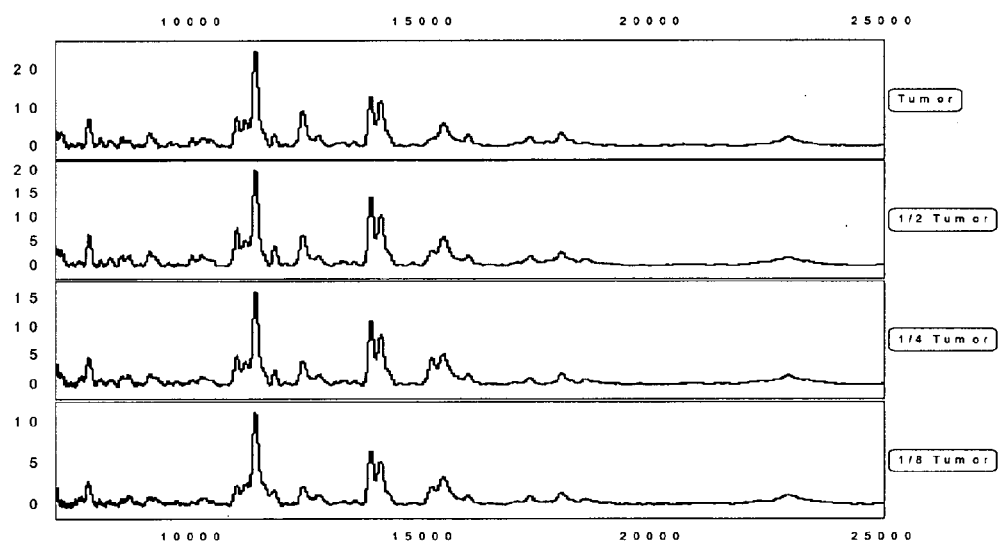
Figure 2b. Different Amounts of Tumor Lysate
Figure 2. Comparative Protein Mass Spectra of Lung Tumor. M/z, mass/charge (in Da).

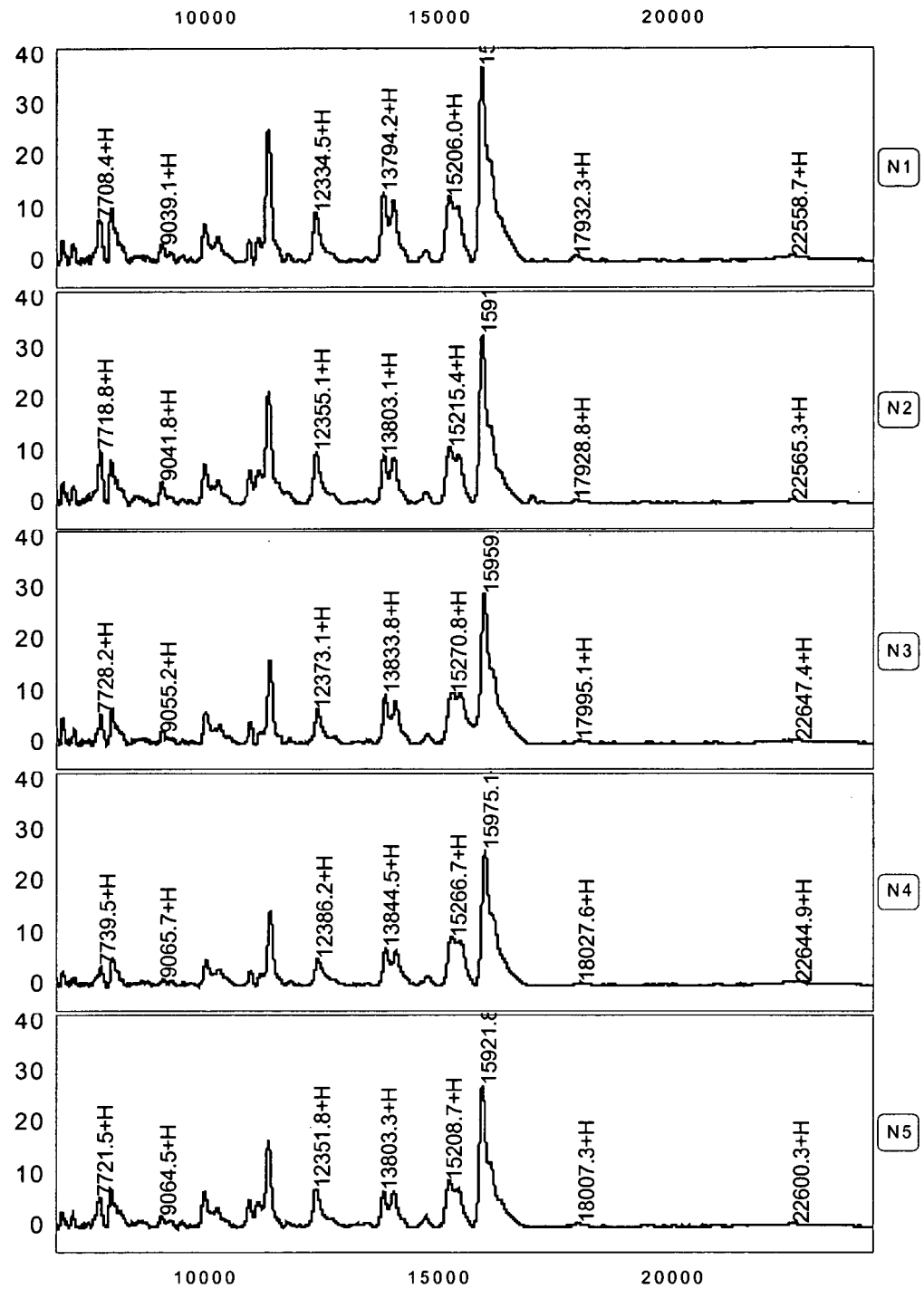
Figure 3a. Reproducibility of SELDI Analysis in Normal Cells.

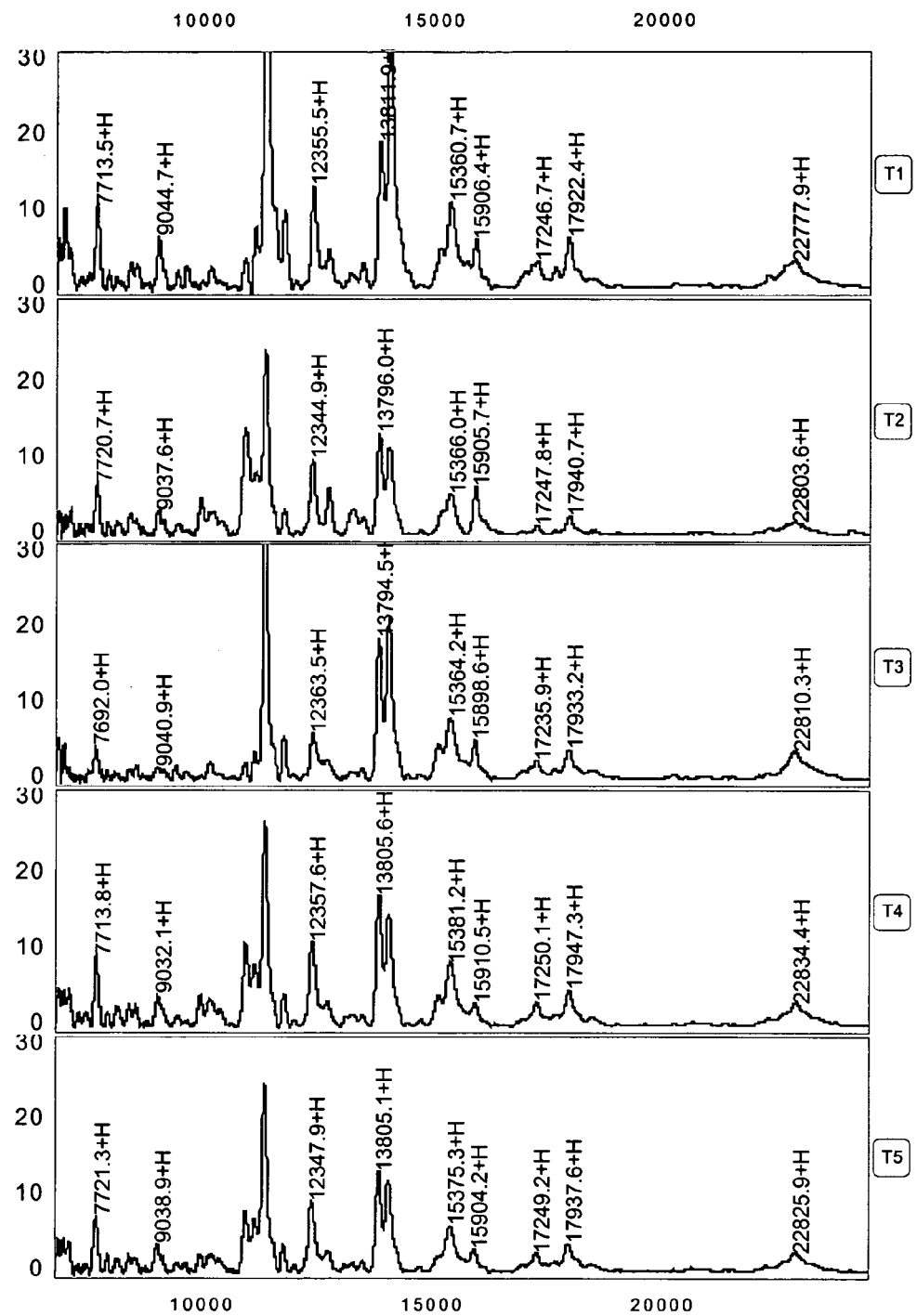
Figure 3b. Reproducibility of SELDI Analysis in Tumor Cells.

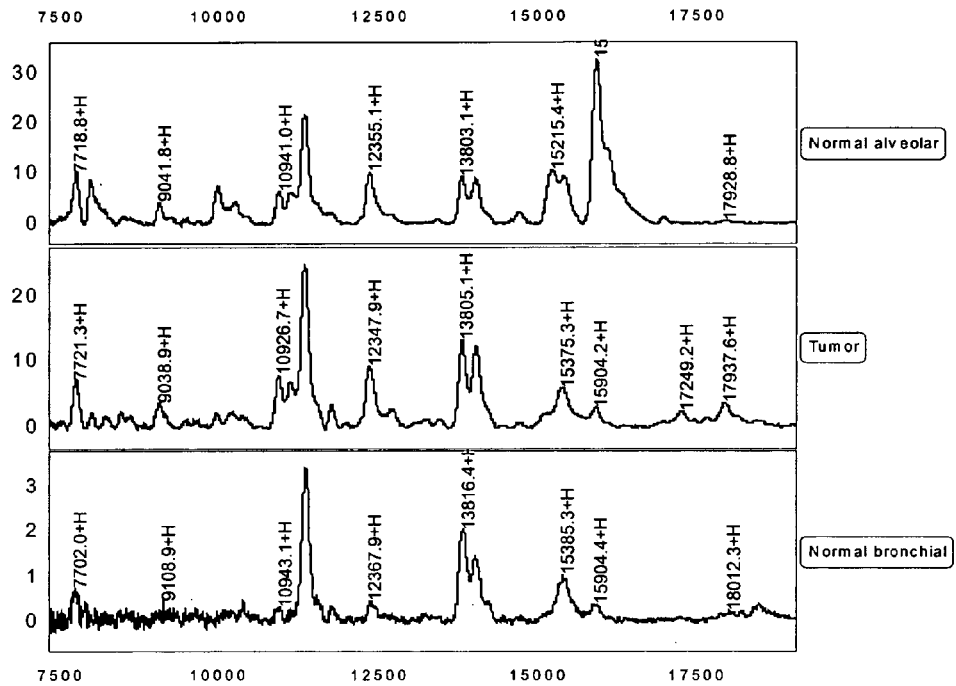
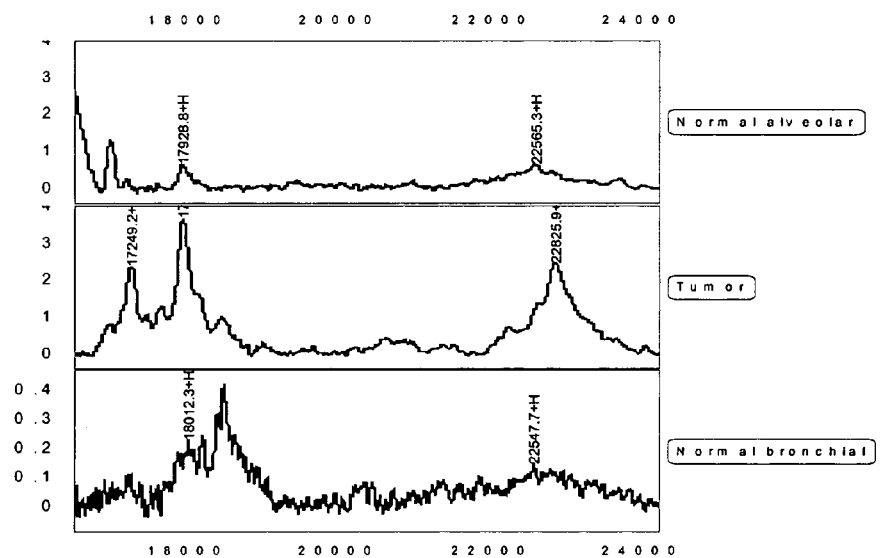
Figure 4. Comparative Protein Mass Spectra of LCM cells from Bronchial Cells.

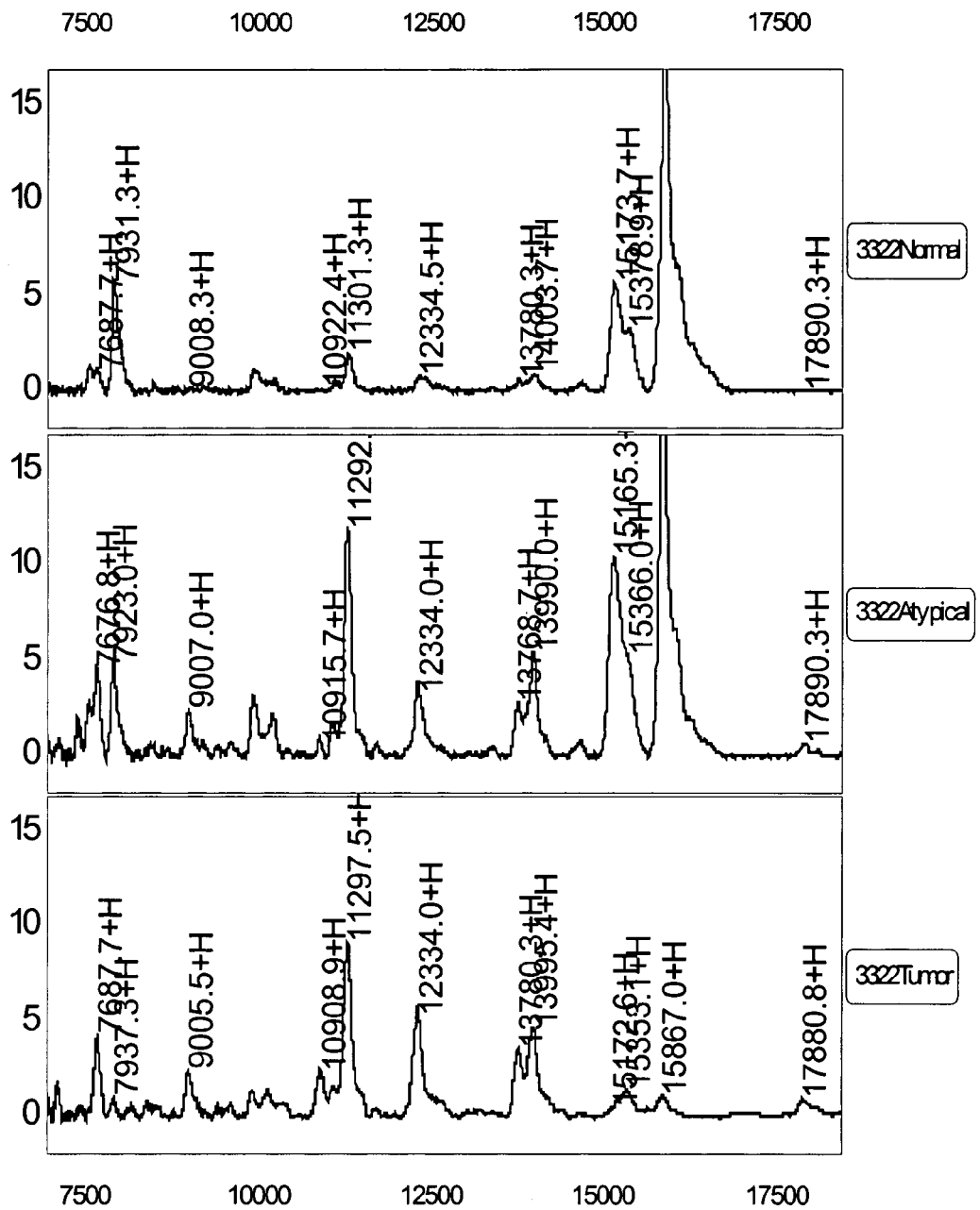
Figure 5a. (Low Mass Range, 7-18 kDa) Protein Mass Spectra of LCM Cells from Adenocarcinoma of the Lung and Adjacent AAH.

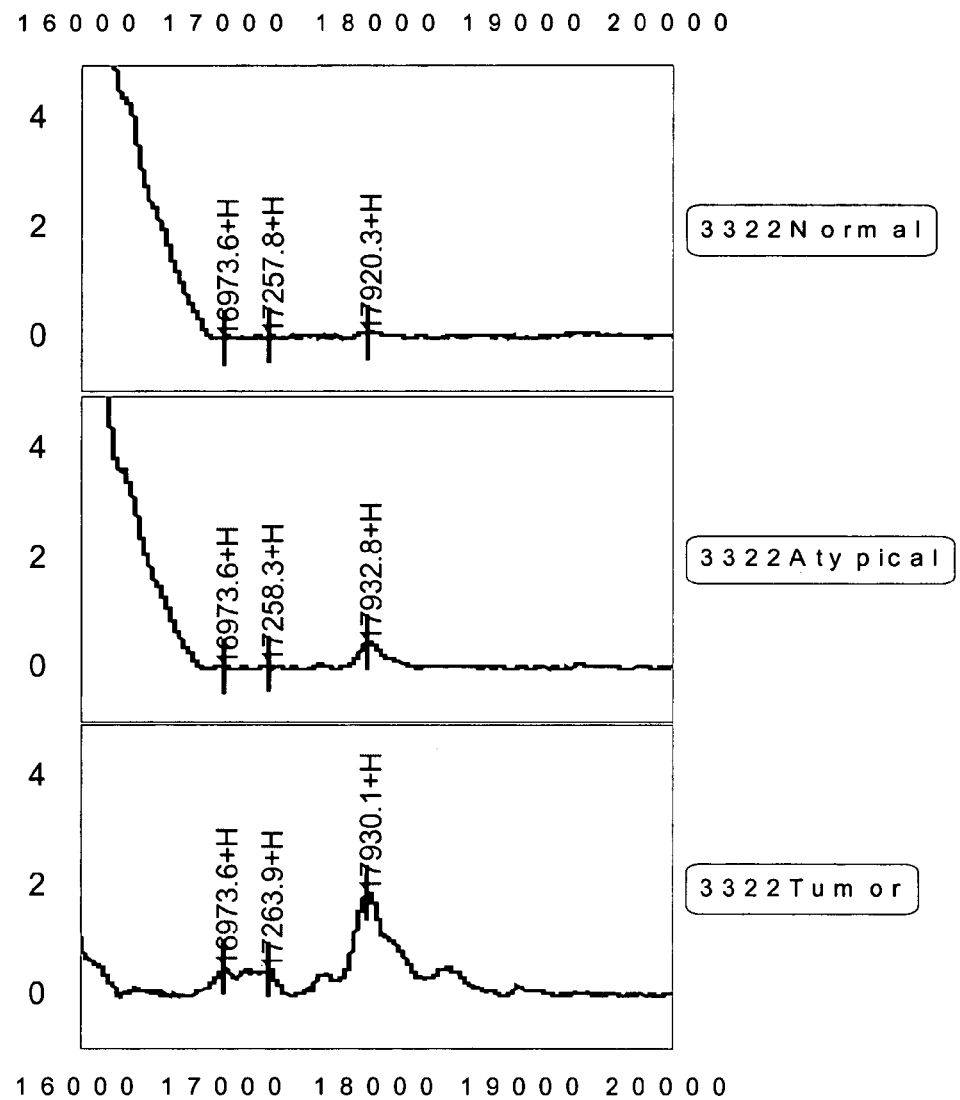
Figure 5b. (High Mass Range, 16 – 20 kDa) Comparative Protein Mass Spectra of LCM Cells from Adenocarcinoma of the Lung and Adjacent AAH.

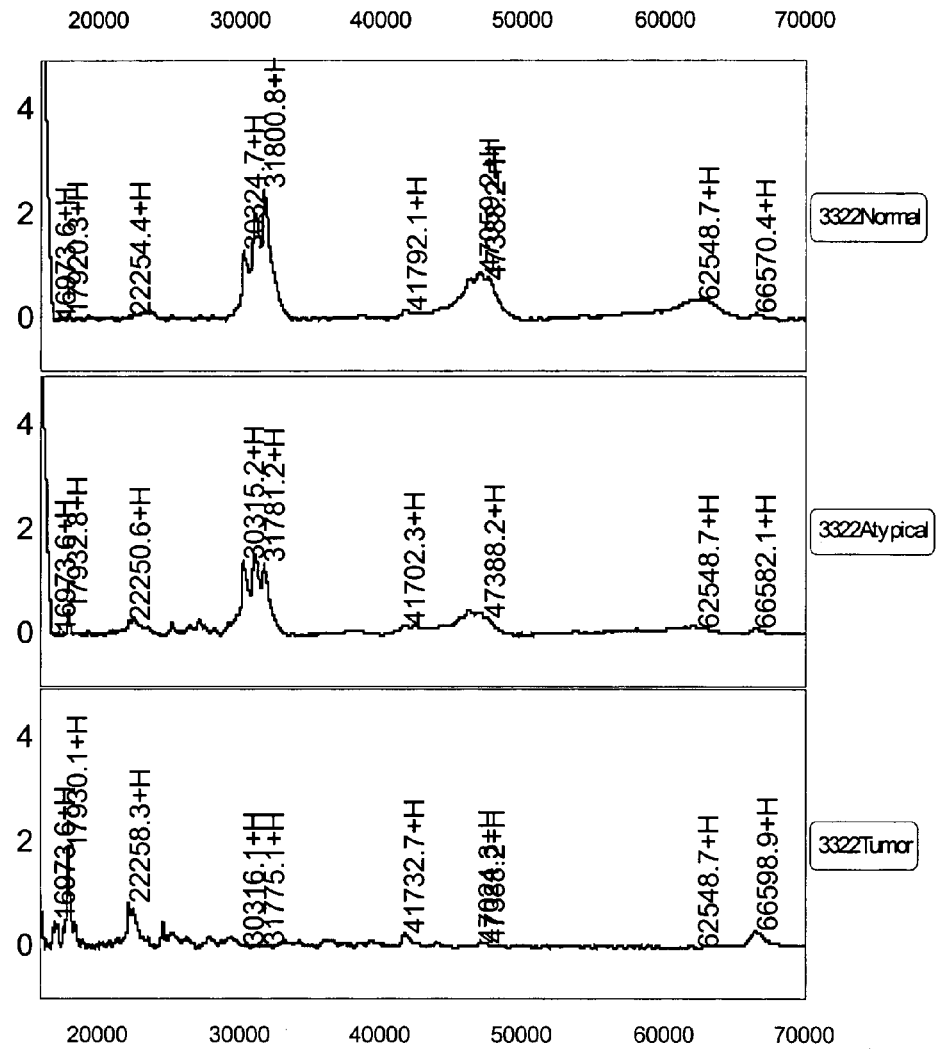
Figure 5c. (High Mass Range, 20-70 kDa) Comparative Protein Mass Spectra of LCM Cells from Adenocarcinoma of the Lung and Adjacent AAH.

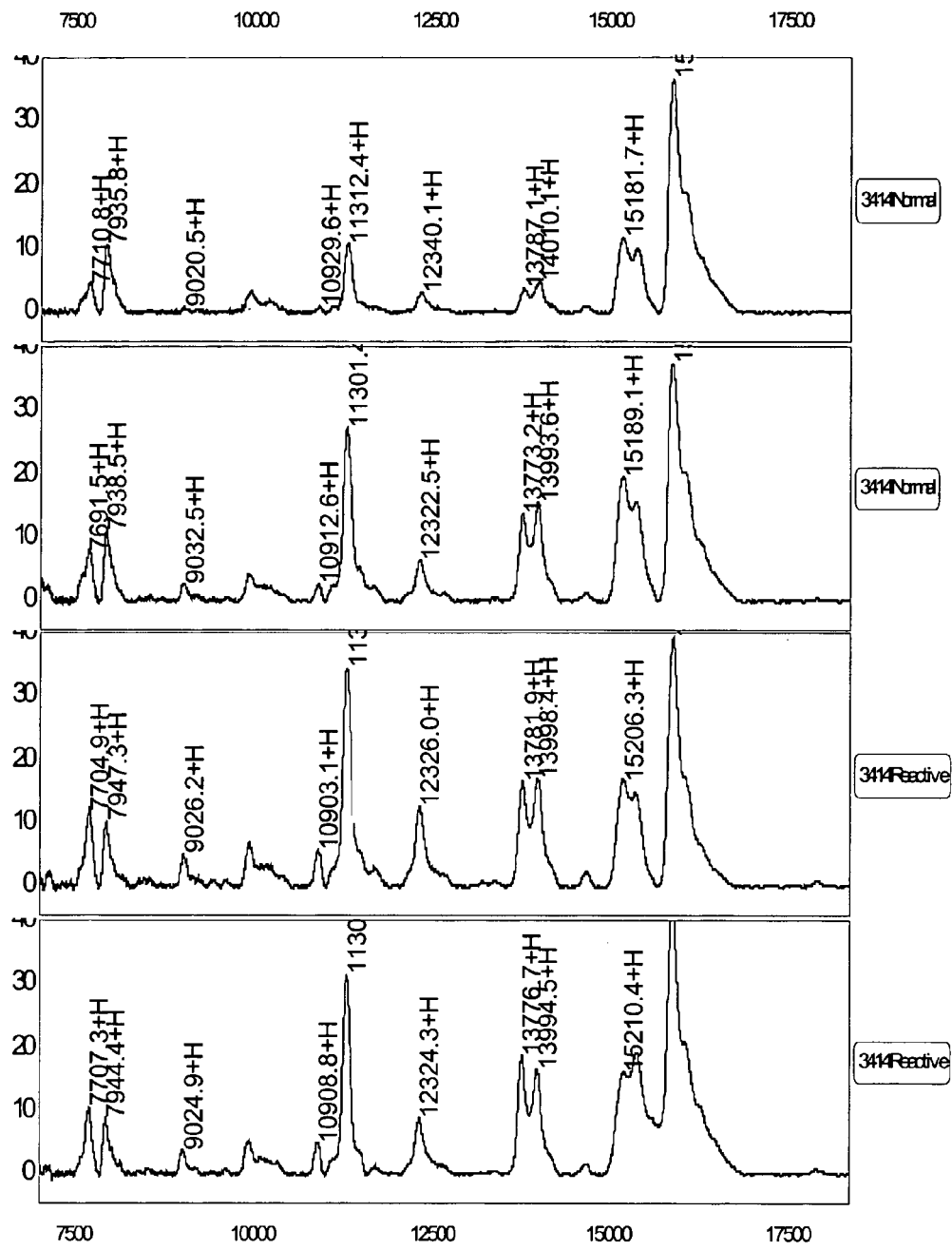
Figure 6a. (Low Mass Range) Comparative Protein Mass Spectra of LCM Cells from Normal Lung Tissue and Reactive Type II Pneumocytes.

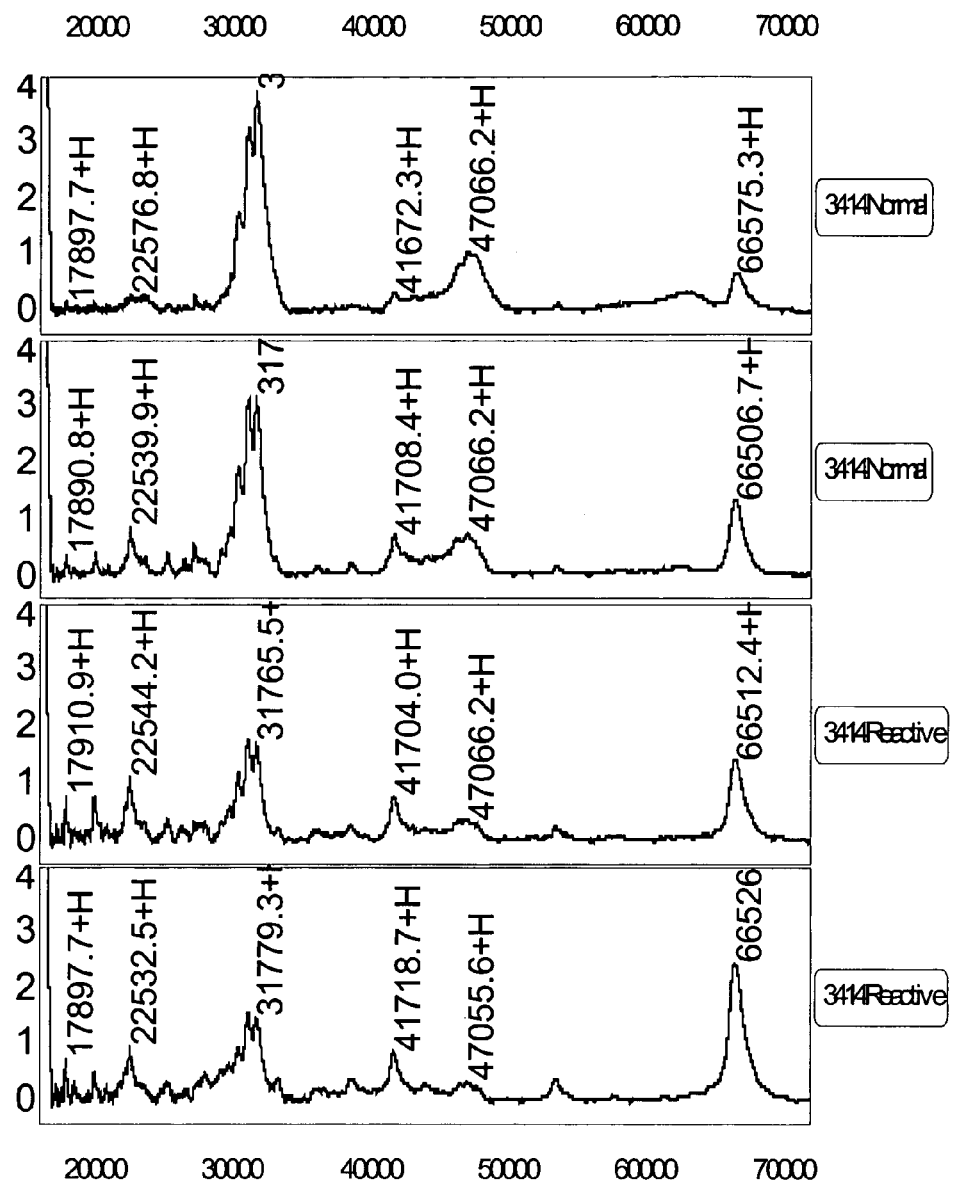
Figure 6b. (High Mass Range) Comparative Protein Mass Spectra of LCM Cells from Normal Lung Tissue and Reactive Type II Pneumocytes.

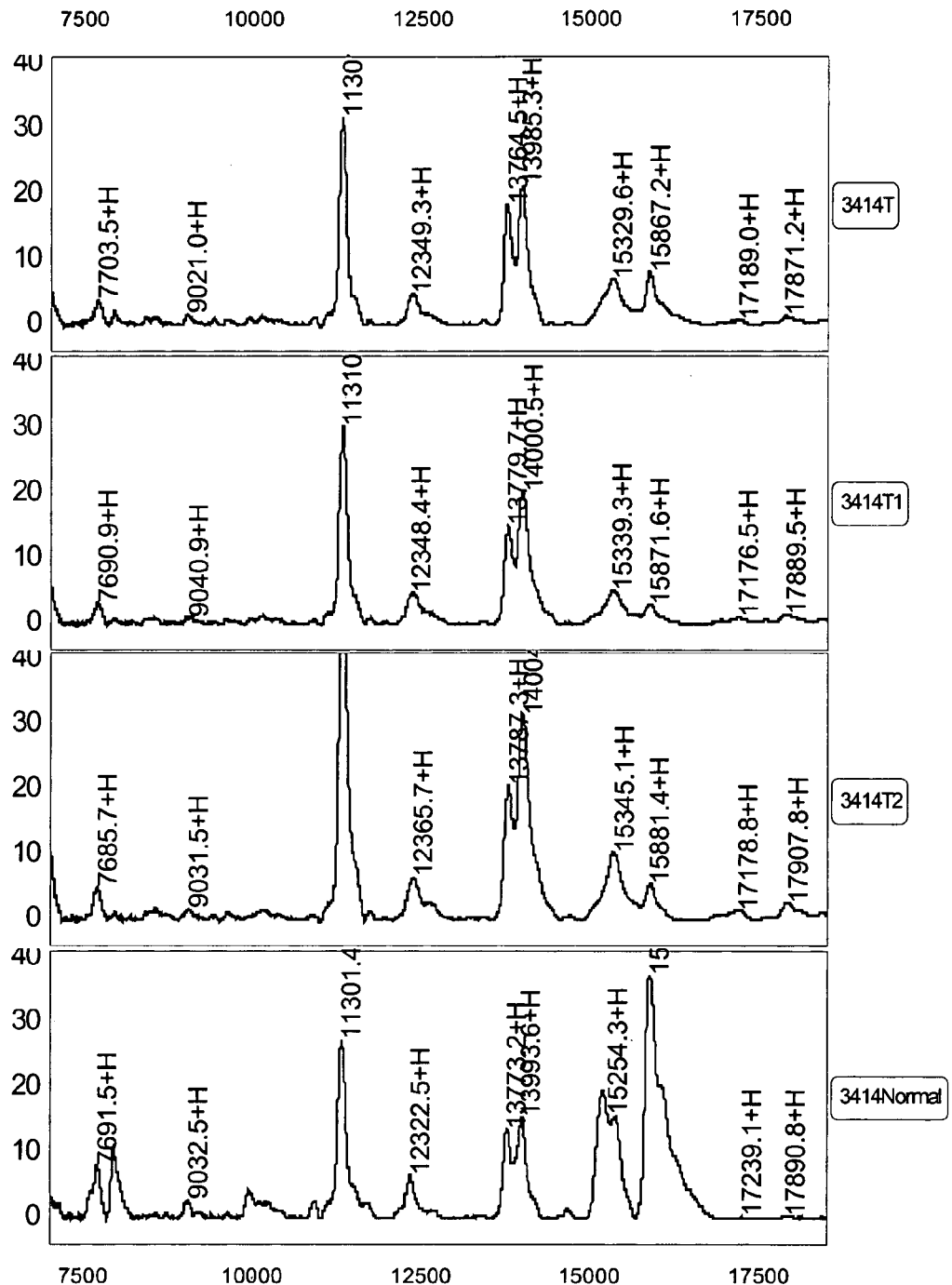
Figure 7a. Comparative Mass Spectra of LCM Cells from Bronchioloalveolar Carcinoma of the Lung (top three lanes) and Adjacent Normal Lung Tissue (bottom lane), (low mass range).

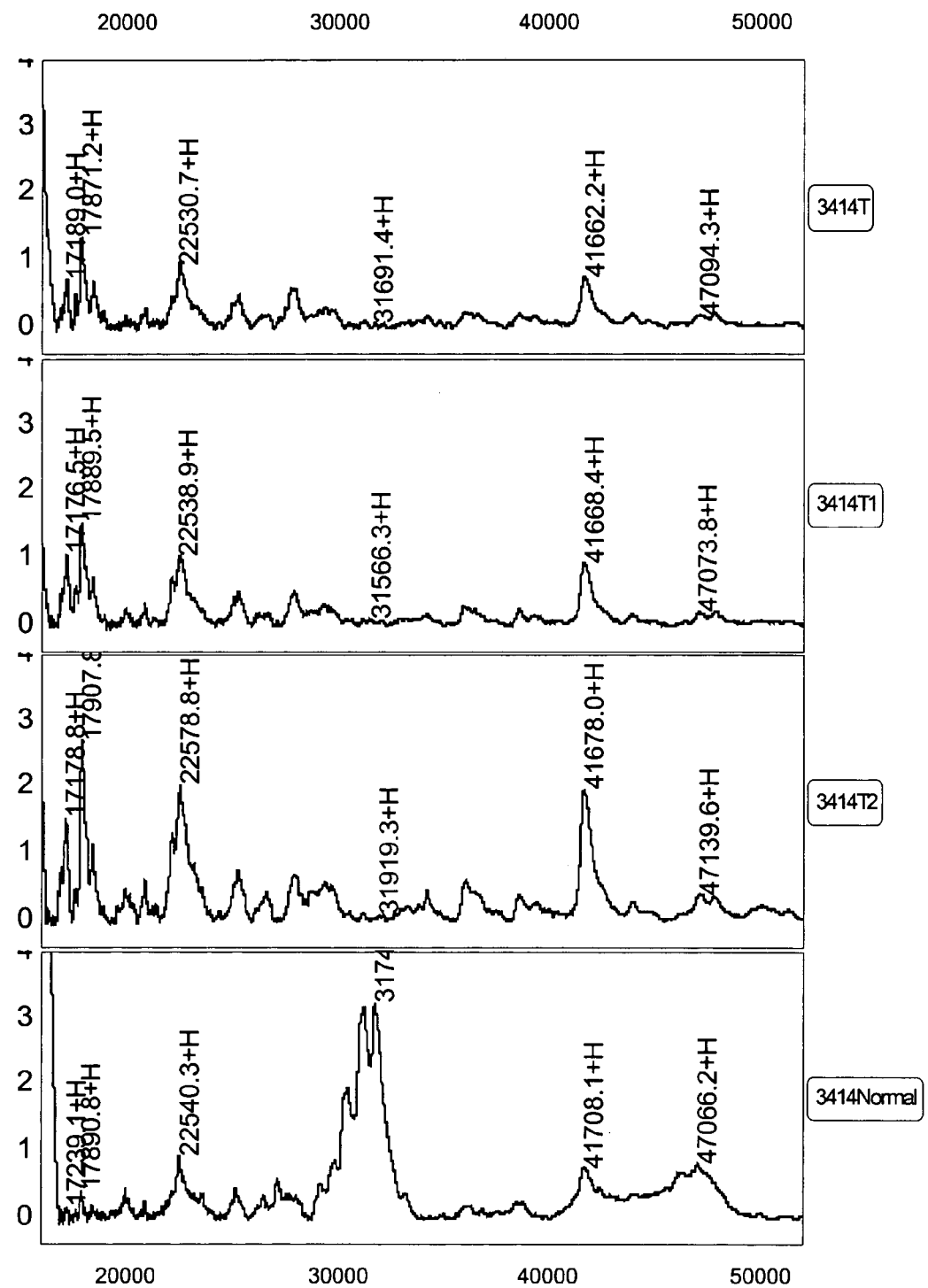
Figure 7b. Comparative Mass Spectra of Tumor and Normal LCM Cells from Bronchioloalveolar Carcinoma of the Lung (top three lanes) and Adjacent Lung Tissue (bottom lane), (High Mass Range).

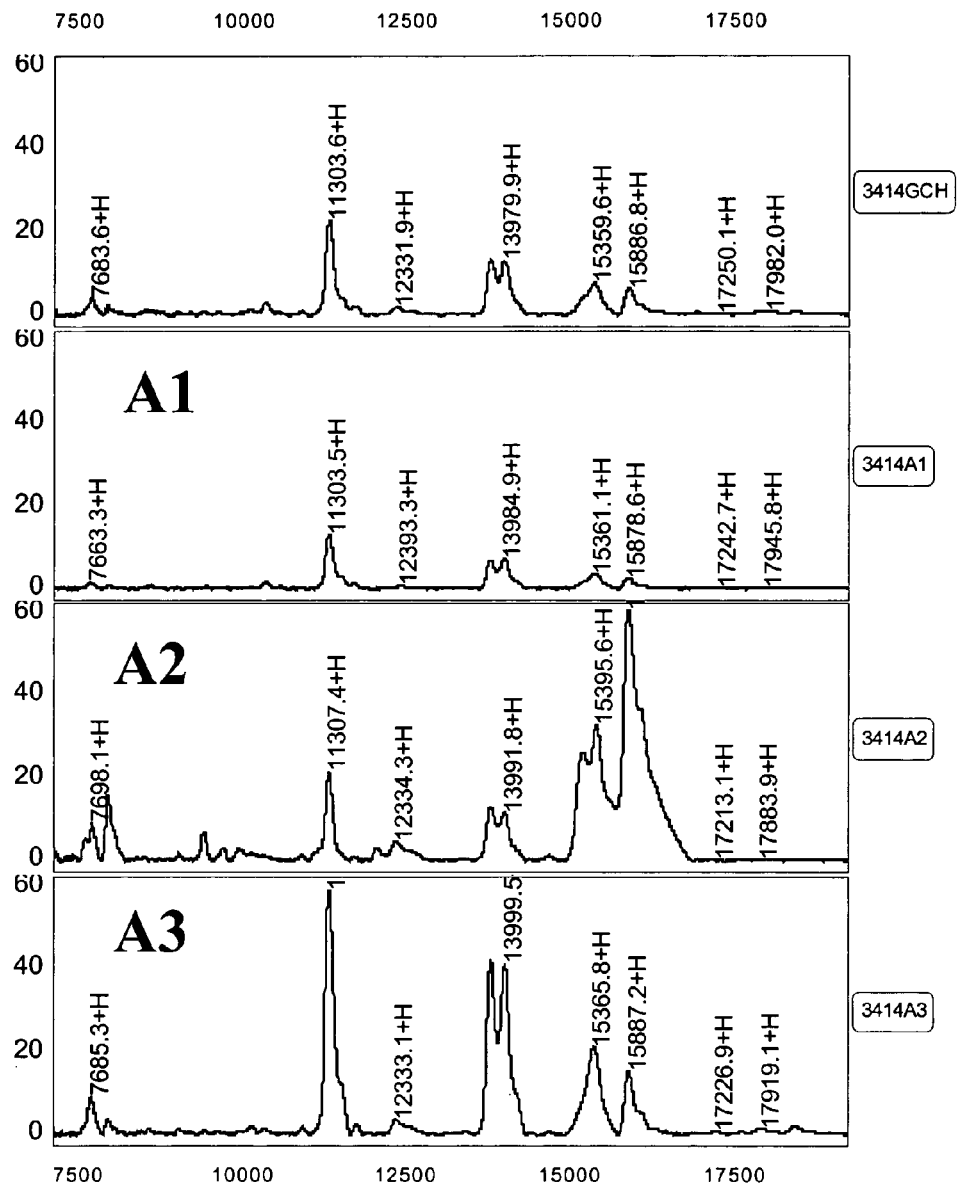
Figure 8a. Comparative Mass Spectra of Atypia and Normal LCM Cells from Bronchioloalveolar Carcinoma of the Lung (bottom three lanes) and Adjacent Normal Lung Tissue (top lane), (Low Mass Range).
A1: Bronchial Squamous Metaplasia
A2: Alveoli Atypia
A3: AAH

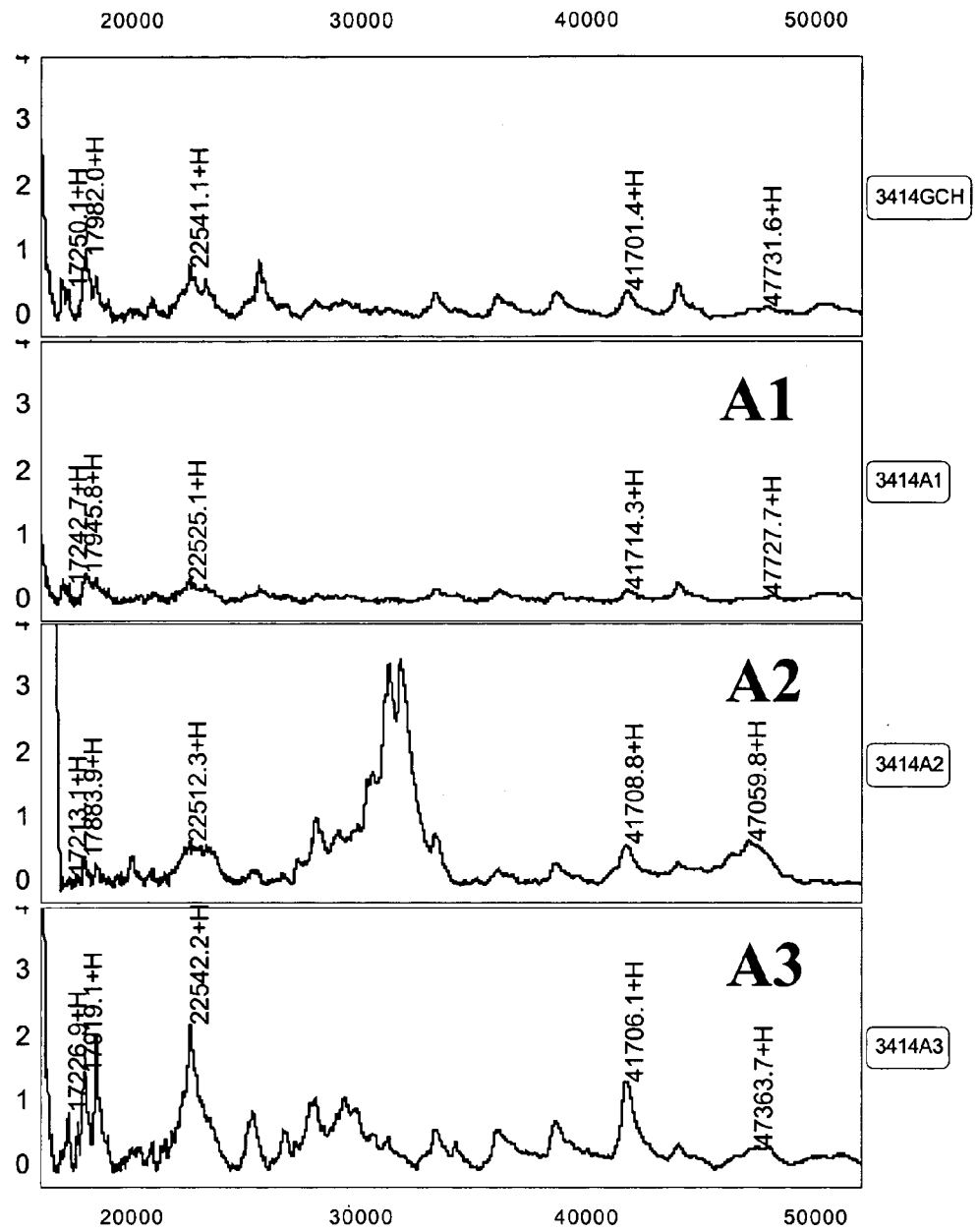
Figure 8b. Comparative Mass Spectra of Atypia and Normal LCM Cells from Bronchioloalveolar Carcinoma of the Lung (bottom three lanes) and Adjacent Normal Lung Tissue (top lane), (High Mass Range).
A1: Bronchial Squamous Metaplasia
A2: Alveoli Atypia
A3: AAH

Fig. 9

Characteristics of samples submitted for SELDI analysis

| Histologic Diagnosis | Case # | Normal Cells | Malignant Cells | Atypical Lesions AAH GCH/Sq. M |
|---|---|---|---|---|
| Adenocarcinoma, well differentiated | #3322 | 3 caps = 6000 alveoli cells | 6 caps = 18000 cells | 2 caps = 500 cells |
| Squamous cell carcinoma, moderately differentiated | #3523 | 8 caps = 16000 alveoli cells 1 cap = 50-80 bronchial epit. cells | 7 caps = 20000 cells | N/A |
| Adenocarcinoma with bronchiolo-alveolar features, moderately differentiated | #3414 | 2 caps = 8000 normal TII celles 2 caps = 6000 reactive TII cells | 2 caps = 8000 cells | 3 caps = 1000 cells |
| Adenocarcinoma with bronchiolo-alveolar features and clear cells features | #3342 | 1 cap = 1000 normal bronc. cells only. No normal alveoli cells for this case. | T1, T2, T3 = papillary region T4, T5 = clear cells features * | 2 caps = 1000 cells |

* Each cap = 1000 laser hits

PROTEIN PROFILING FOR PREMALIGNANT TISSUE

PRIORITY

This application claims priority from U.S. Provisional Patent Application Ser. No. 60/369,792 filed Apr. 4, 2003 entitled "Distinct protein profiling specific for lung tumors and premalignant lung lesions by SELDI mass spectrometry" the specification of which is incorporated herein by reference.

BACKGROUND OF INVENTION

1. Field of Invention

This invention relates to a method of diagnosing cancer and more specifically, for detecting premalignant cells.

2. Background

Lung cancer is the leading cause of cancer death in both men and women in the United States, accounting for an estimate 160,000 deaths per year. While male incidence is beginning to fall, female lung cancer incidence is increasing with a predominance of peripheral carcinomas (adenocarcinoma). Screening for frankly malignant lung cancer cells exfoliated from the airway epithelium has not resulted in frequent early-stage lung cancer detection and cure. Several lung cancer detection trials showed no reduction in lung cancer mortality among high-risk cohorts of smokers screened with sputum cytology and radiographic techniques compared with radiographic screening alone. These studies concluded that sputum cytopathology, while highly specific, is not sufficiently sensitive for lung cancer screening.

Larger airway epithelial lesions of sufficient size to alter radiographic contrast may be detected by new imaging technology, such as low-does multi-slice helical computerized tomography (CT) scans. Helical CT has been able to detect peripherally located nodules, especially those less than 1-2 cm. Preliminary results of helical CT screening at the H. Lee Moffitt Cancer Center and Research Institute at the University of South Florida have shown that at least 50% of CT-detected lung cancers are early-stage, potentially curable peripheral adenocarcinomas. However, 90% of CT-detected lesions are not cancerous (false positives).

Traditionally, molecular analysis has been performed on biopsies of whole tissue. Cellular heterogeneity of tissue specimens has confounded assessment of analyte levels of specific cell types. Laser capture microdissection (LCM) technology can now collect homogeneous populations of intact cells from solid tissue sections and cell smears for molecular analysis. Cells can be collected based on either morphology or immunohistologic features. LCM enables the user to procure pure cells from stained heterogeneous tissue under direct high-power microscopic visualization. The cells of interest are transferred to a polymer film that is activated by laser pulses. The exact morphology of the procured cells (with intact DNA, RNA, and proteins) is retained and held on the transfer film. Direct visualization of the captured cells, with their histology intact assures that the correct population of cells is selected. The ability of LCM to procure homogeneous cell subpopulations of normal, premalignant, and malignant cell types has had a significant impact on genomics and proteomics cancer research.

Significant technological advances in protein chemistry in the last two decades have established mass spectrometry as an indispensable tool for protein study, including discovery, identification (peptide mapping, sequencing), and structural characterization. Ciphergen Biosystems, Inc. (Fremont, Calif.) has developed ProteinChip® technology that utilizes surface enhanced laser desorption/ionization time-of-flight mass spectrometry (SELDI-TOF MS) to facilitate protein profiling of complex biological mixtures. References relating to the SELDI-TOF MS technology include U.S. Pat. No. 6,294,790 entitled "Secondary ion generator detector for time-of-flight mass spectrometry"; U.S. Patent Application No. 20010014461A1 entitled "Retentate chromatography and protein chip arrays with applications in biology and medicine"; U.S. Patent Application No. 20020060290A1 entitled "Method for analysis of analytes by mass spectrometry"; U.S. Patent Application No. 20020137106A1 entitled "Detection of biological pathway components"; U.S. Patent Application No. 20020138208A1 entitled "Method for analyzing mass spectra"; U.S. Patent Application No. 20020142343A1 entitled "Retentate chromatography and protein chip arrays with applications in biology"; U.S. Patent Application No. 20020155509A1 entitled "Retentate chromatography and protein chip arrays with applications in biology"; U.S. Patent Application No. 20020177242A1 entitled "Retentate chromatography and protein chip arrays with applications in biology and medicine"; U.S. Patent Application No. 20020182649A1 entitled "Methods for protein identification, characterization and sequencing by tandem mass spectrometry"; U.S. Patent Application No. 20030008412A1 entitled "Plate alignment and sample transfer indicia for a multiwell multiplate stack and method for processing biological/chemical samples using the same"; U.S. Patent Application Nos. 20030017464A1 and 20030032043A1 both entitled "Latex based adsorbent chip"; and U.S. Patent Application No. 20030054367A1 entitled "Method for correlating gene expression profiles with protein expression profiles" all assigned to Ciphergen Biosystems, Inc. and all incorporated herein by reference.

The ProteinChip® technology advanced by Ciphergen Biosystems utilizes biochip arrays to capture individual proteins or groups of proteins with common biochemical properties such as hydrophobicity or charge from complex mixtures. These retained proteins are subsequently resolved directly by time-of-flight mass spectrometry. It is fast, sensitive and scalable for high-throughput sample processing. These characteristics make SELDI technology suitable for the studies of cancer development from premalignant lesions when minimal, multiple protein changes may have pathodiagnostic significance.

SUMMARY OF INVENTION

Coupling SELDI technology with LCM of enriched cell populations provides a method to generate specific protein profiles of frankly malignant lung cancer cells, and cells in intermediate stages between normal and cancer. The present invention stems from the inventors' discovery that proteins critical to lung neoplastic progression can be identified through the changes in peptide/protein mass spectral patterns detected by SELDI analysis of malignant lung tumors and premalignant airway epithelium lesions showing neoplastic transformation. For the first time, it is feasible to characterize malignant and premalignant lung lesions based on their unique protein mass spectral patterns.

The present invention is a method for early detection of cancer including the steps of identifying tissue from asymptomatic individuals, gathering a substantially homogenous cell population from the tissue by laser capture microdissection (LCM), analyzing the cell population with mass spectrometry and identifying predetermined peaks in the mass spectrometry associated with an overexpression of proteins in premalignant cells. The mass spectrometry is done by timeof-flight technology, such as a SELDI ProteinChip® mass reader available from Ciphergen Biosystems, Fremont, Calif. Tissue from asymptomatic individuals may be identified by helical computed tomography. The tissue is retrieved and cryopreserved before sectioning. The LCM may be performed with an appropriate LCM apparatus including an AutoPix™ Automated Laser Capture Microdissection System or PixCell® IIe Laser Capture Microdissection System from Arcturus Engineering, Mountain View, Calif. Predetermined peaks discovered in the present invention include those at approximately 12348, 13794, 14010, 17250, 1726.8, 17922, 17930, 22250 and 22810 Da which constitute biomarkers for premalignant lung cells.

An alternative embodiment of the invention includes a method for identifying premalignant cell biomarkers. The steps include identifying tissue known to be normal, identifying tissue known to be premalignant, and identifying tissue known to be malignant. A first substantially homogenous cell population is gathered from the normal tissue by laser capture microdissection. A second substantially homogenous cell population is gathered from the premalignant tissue by laser capture microdissection. A third substantially homogenous cell population is gathered from the malignant tissue by laser capture microdissection. Each resulting peptide profile is then comparatively analyzed by differentiating the peaks in the mass spectrometry to discern new biomarkers.

By identifying premalignant cells before they become tumors, cancer may be preemptively treated by gathering a substantially homogenous cell population from asymptomatic tissue by LCM, analyzing the population with mass spectrometry, identifying predetermined peaks in the mass spectrometry associated with an overexpression of proteins in premalignant cells and administering chemopreventive agents responsive to the presence of premalignant cells.

This invention advances the type of information provided by SELDI technology for early lung cancer detection. Lung tumor specimens from patients treated at Moffitt Cancer Center at the University of South Florida were laser capture microdissected to obtain pure cell populations from normal lung, premalignant lesions and malignant tumors. SELDI mass spectrometry was used to identify protein profiles in each epithelial cell type. An objective of the invention was to identify protein profiles that could be used to differentiate malignant cells from non-malignant, and particularly to find early protein alterations representing the initiation of neoplastic transformation in respiratory epithelium.

References in the field include "Use of proteomic patterns in serum to identify ovarian cancer." Petricoin, E., Ardekani, A., Hitt, B., et al. The Lancet 2002, 359, 572-577 and "A database of protein expression in lung cancer." Oh, J., Brichory, F., Purays, E., et el. Proteomics 2001, 1, 1303-1319. The present invention enables those of ordinary skill in the art to obtain unique information on lung cancer specific and premalignant lung lesions associated protein profiles (proteomic patterns) obtained with SELDI mass spectrometry data analysis after laser assisted cell capturing. This permits the analysis of protein profiles from "pure" specific respiratory cell populations reflecting stages of lung cancer development.

This is improvement over the prior art because the isolation of complex lung tumor tissue sections enables one to perform sensitive SELDI mass spectrometry and validate even minor changes in protein expression specifically in malignant lung tumor cells and premalignant lung lesions. The SELDI technology has advantages over the 2-D gel approach due to the time and practical laboratory efforts to perform the proteomic analysis and data analysis using bioinformatic databases.

This invention with the use of "pure" single specific respiratory cell populations is an improvement versus the approach to use the patients serum.

BRIEF DESCRIPTION OF DRAWINGS

For a fuller understanding of the nature and objects of the invention, reference should be made to the following detailed description, taken in connection with the accompanying drawings, in which:

FIG. 1 shows an array of representative sections from lung tumors of differing cell types (before and after laser capture microdissection), premalignant (AAH) lung tissue and normal lung tissue.

FIG. 2 shows comparative mass/charge spectrums of normal (FIG. 2A) and tumor lysates (FIG. 2B) in addition to the loss of spectrum detail in lysates with lower numbers of cells.

FIG. 3a shows mass/charge spectrum of normal and squamous lung cells to demonstrate the reproducibility of the analysis.

FIG. 3b shows mass/charge spectrum of squamous lung cancer cells to demonstrate the reproducibility of the analysis.

FIG. 4 shows tumor-associated changes in the low mass/charge range for squamous lunch cancer and normal bronchial cells.

FIG. 5a shows tumor-associated changes in the low mass/charge range for normal, atypical, and adenocarcinoma cells.

FIG. 5b shows tumor-associated changes in the high mass/charge range at the 16000 to 20000 dalton scale for normal, atypical, and adenocarcinoma cells.

FIG. 5c shows tumor-associated changes in the high mass/charge range for normal, atypical, and adenocarcinoma cells.

FIG. 6a compares spectrums in the low mass/charge range for normal and reactive type II cells adjacent to bronchioloalveolar carcinoma of the lung.

FIG. 6b compares spectrums in the high mass/charge range for normal and reactive type II cells adjacent to bronchioloalveolar carcinoma of the lung.

FIG. 7a shows tumor-associated changes in the low mass/charge range for normal and bronchioloalveolar carcinoma cells.

FIG. 7b shows tumor-associated changes in the high mass/charge range for normal and bronchioloalveolar carcinoma cells.

FIG. 8a shows comparative mass spectrums of tumor-associated changes in the low mass/charge range for normal, atypical, and bronchioloalveolar carcinoma cells FIG. 8b shows comparative mass spectrums of tumor-associated changes in the high mass/charge range for normal, atypical, and bronchioloalveolar carcinoma cells.

FIG. 9 is a table showing characteristics of samples submitted for SELDI analysis.

DETAILED DESCRIPTION

Figure 10:
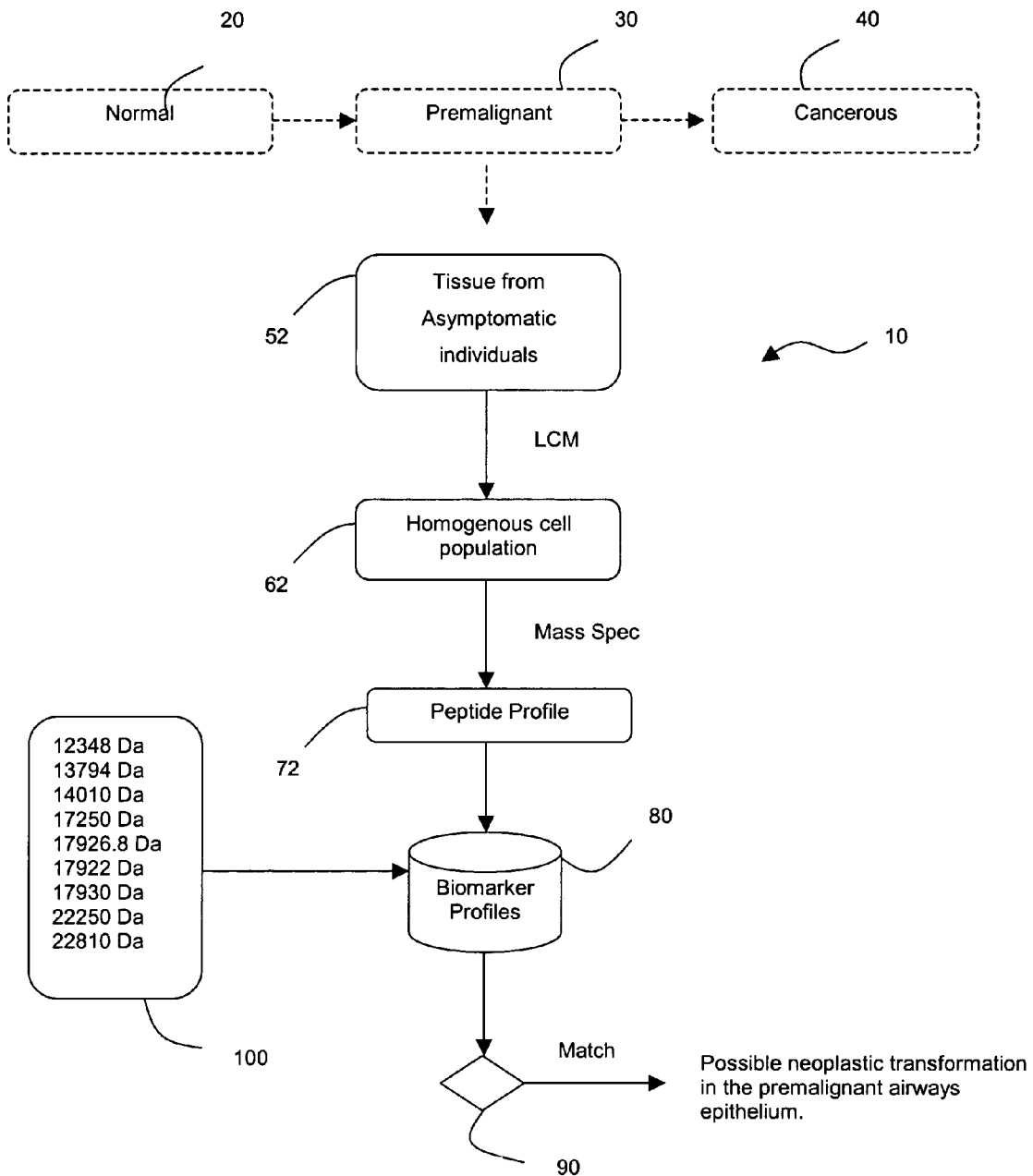
FIG. 10 is a diagrammatic view of an embodiment of the invention for detecting premalignant cells.

Lung tumor specimens from "Cohort of smokers" study patients treated at Moffitt Cancer Center at the University of South Florida were laser capture microdissected to obtain pure cell populations from frozen sections of normal lung, premalignant lesions and malignant tumors. SELDI mass spectrometry was used to identify protein profiles in each epithelial cell type.

LCM was performed with 15000-20000 laser hits to each specimen. Cell lysates were prepared from 45 samples procured from 4 resected lung tumors (adenocarcinoma, squamous cell carcinoma, adenocarcinoma with BAC features and adenocarcinoma with BAC papillary and clear cells features) selected for analysis (FIG. 7), and were applied to IMAC-Cu Chips. Chips were read on a PBS II ProteinChip Reader at low (220) and high (260) laser intensities. Clustering software was applied in the analysis of identified protein peaks.

Alterations in proteins are expressed during lung cancer development. The representative peaks of proteins were found overexpressed in the lung tumor cells and in some of the atypical premalignant lung lesions. These peaks were not detected in any of the normal cell suggesting proteomic alterations occurring in early stages of the disease.

TABLE 1

Protein peaks and intensities of expression in lung tumor and cells from AAH lesions expressed in protein mass/intensity.

| Normal Cell Type | Malignant Cell Type | AAH Cell Type |
|---|---|---|
| 12353.6/2.01 | 12348.2/6.09* | |
| 13803.3/3.91 | 13794.2/10.34* | |
| 14010.3/2.44 | 14010.3/12.24* | 14000.0/8.90* |
| 15208.7/4.97* | 15208.7/1.38 | |
| 15921.8/15.56* | 15910.5/1.53 | |
| 17250.0/0.00 | 17250.0/1.63* | 17250.0/0.66* |
| 17922.4/0.12 | 17922.4/2.52* | 17926.8/0.52* |
| 22777.9/0.20 | 22810.9/2.07* | |
| 66633.2/2.84* | 66576.6/0.13 | |

*P = 0.001, Wilcoxon Signed Ranks Test.

Highlighted proteins are of similar molecular weight range across different study cases, independent of tumor histology type, and showed that intensity of expression of six peaks is significantly high in malignant cells compared with normal cells for all cases. Six peaks detected in the mass spectra were significantly higher in tumor cells compared with normal cells. These peaks were: 12348, 13794, 14010, 17250, 17922 and 22810 Da. Two peaks at 17-18 kDa mass range and peak at 14 kDa were also increased in premalignant cells from AAH lesions.

LCM PROTOCOL: Laser capture microdissection in general is well-known in the art as provided in U.S. Pat. Nos. 5,859,699 issued Jan. 12, 1999, 5,985,085 issued Nov. 16, 1999, 6,157,446 issued Dec. 5, 2000, 6,184,973 issued Feb. 6, 2001, 6,215,550 issued Apr. 10, 2001, 6,469,779 issued Oct. 22, 2002 and 6,495,195 issued Dec. 17, 2002 all of which are incorporated herein by reference.

Frozen tissue specimens were sectioned at 10 μm in a cryostat, mounted on uncoated glass slide and stored at 4° C. in 100% ethanol until the day of the LCM.

H&E stain was performed on one of every 5 frozen tissue sections to assure visual discrimination of specific cell populations procured by LCM. Laser "capturing" was performed on frozen sections stained lightly only with hematoxylin. Each cell population is estimated to be ~98% "homogeneous" as determined by microscopic visualization of the captured cells. LCM was performed with capture 20000-25000 cells from each lung tumor case.

Malignant cells and morphologically recognizable atypical premalignant cell populations were transferred separately. Cell samples were frozen immediately at −70° C., and on the same day were sent on dry ice to Biomarker Discovery Center of Ciphergen Biosystems, Inc., Malvern, Pa.

Lysis and ProteinChip protocol: LCM caps: ~1000 laser hits (1,000 to 2,000 cells). Lysis buffer: 6 M Guanidine HCI in 0.1 M Hepes, pH 7.4, 1% Triton X100, Roche Complete protease inhibitors. To LCM cap, added 4 μl lysis buffer and incubated one hour at RT in humidity chamber. Samples were transferred to 500 μl tubes and the caps rinsed with 10 μl 0.1 M Hepes, pH 7.4. Combined 24 μl samples were applied to IMAC-Cu Chips in a bioprocessor and incubated at RT with shaking for 1 hr. Spots were washed 3× with 200 μl PBS and 2× with 200 μl $H_2O$.

EAM applied, two 0.5 ml additions of saturated SPA. Chips were read on a PBS II ProteinChip Reader at low (220) and high (260) laser intensities.

Mass Analysis

Each spot was interrogated twice, with separate optimization for low (5-12 kDa) and high (20-100 kDa) mass ranges. Mass optimization windows were set for low-mass and all of the spots on one array were analyzed. Laser power and number of shots were optimized manually. The mass optimization window was reset for the high-mass range and the samples were reanalyzed for high molecular weight proteins. Positive samples (malignant and premalignant cell lystates) and controls (normal cells) were run concurrently on the same array. For the calculation of protein peaks numbers/instensities resolved at different laser intensities, the ProteinChip Software, Version 3.0 from Ciphergen Biosystems was used. External calibration was performed using bovine insulin (5733.6 Da), bovine cytochrome C (12230.9 Da), and bovine serum albumin (66410 Da) as standards.

Data Analysis

SELDI mass spectral analysis was correlated with morphology from lung cancer, cells intermediate in lung cancer progression, or normal epithelial cells. Protein peaks (profiles) were considered to be differentially expressed in malignant/premalignant lung, if statistically significant differences in their frequency and/or intensity were observed, compared with normal lung epithelium. The non-parametric Mann-Whitney test and Wilcoxon Signed Ranks Test were used to compare statistically significant differences in intensity data at various protein peaks for different cell types.

Detection of Protein Profiling Specific for Lung Cancer Optimization of Sample Size The number of LCM cells required to maintain a consistent signal compared with background was first standardized. FIG. 2 shows examples of protein mass spectra of normal and malignant lung samples. The cell lysates from one sample of either tumor (FIG. 2b) or normal (FIG. 2a) cells was diluted to ½, ¼, ⅛, and 1/16 concentration (from top to bottom) and spotted individually (equivalent to 1000, 500, 250, and 125 laser hits). The results for samples equivalent to 500-1000 laser hits showed consistent signal strength, suggesting that 500-1000 laser hits is a minimum sample size for this method as loss of detail was observed at lower levels of cells.

Reproducibility of Protein Detection Using The SELDI-TOF MS Technology

Multiple samples of normal and tumor cells from patient 3523 were run five times using identical protocols to evaluate the reproducibility within sample (FIG. 3a, 3b). Subsequent samples were processed in duplicate to confirm reproducibility in detecting lung cancer proteins. Repeatable peaks in low mass range across five specimens are shown for patient 3523 (squamous cell carcinoma of lung), to confirm reproducibility in resolving the lung tumor proteins. The intra-assay reproducibility, i.e., the mean mass and S.D. for detected protein peaks are shown for different cell types (tumor and normal).

TABLE 2

SELDI intra-assay reproducibility of five runs samples from patient 3523.

| Protein Peaks (Da, mean +/− S.D.) | Coefficient of variation |
|---|---|
| Normal Lung | |
| 7723.28 +/− 11.53 | 0.1493148 |
| 9053.26 +/− 12.42 | 0.1371511 |
| 12360.14 +/− 19.99 | 0.1617828 |
| 13815.78 +/− 21.97 | 0.1590649 |
| 15223.52 +/− 32.37 | 0.2125213 |
| 17978.22 +/− 45.05 | 0.2506109 |
| 22603.32 +/− 42.18 | 0.1866218 |
| Malignant Tumor | |
| 7712.26 +/− 11.91 | 0.1544212 |
| 9038.84 +/− 4.62 | 0.0511649 |
| 12353.88 +/− 7.51 | 0.0607647 |
| 13802.62 +/− 7.26 | 0.0526084 |
| 15369.48 +/− 8.49 | 0.0552382 |
| 15905.08 +/− 4.31 | 0.0270916 |
| 17245.94 +/− 5.76 | 0.0334069 |
| 17936.24 +/− 9.28 | 0.0517672 |

This data shows that reproducibility (coefficient of variation) of protein detection using the SELDI-TOF MS technology is acceptable. Similar highly reproducible SELDI mass spectrometry data within each peak detected in lung tumor/normal tissue samples were confirmed by third-party data.

Comparison of Protein Profiles from LCM'S Malignant, Premalignant and Normal Lung Cells Lysates from tumor, atypical, and normal cells were compared side by side for protein mass spectral analysis. Representative measured mass/charge ratios of specific proteins and their corresponding intensities are shown for each patient from the study set in FIGS. 4-8. When protein profiles for each patient were compared, they revealed similar change in several peaks expressed across different patients. Intensities for all the peaks shown in the mass/charge spectra graphs were generated by pooling all the spectra together for each individual patient and normalizing them to total ion current. Intensities for six peaks detected in the mass/charge spectra were significantly higher in tumor cells compared with normal cells. These peaks were: 12348, 13794, 14010, 17250, 17922, and 22810 Da. Three peaks at 17-23 kDa mass/charge range from tumor cells showed marked increases when compared with normal cells. The peak at 17250 Da was not detected in any of the normal respiratory epithelial cells with a limit of detection of 5% of tumor levels. This peak appears to be present at low levels in the atypical cell samples (Table 1). Three peaks at 15208.7, 15910.5 and 66576.6 Da mass range from tumor cells were significantly decreased in tumor cells compared with normal cells.

These data from SELDI analysis of cell type, specific malignant/premalignant lung lesions defined a "malignant" lung protein profile, as illustrated in Table 1. Proteins noted in bolded font are of similar molecular weight range across different study cases, independent of tumor histology type, and show that intensity of expression of six peaks is significantly higher in malignant cells compared with normal cells for all cases. Two peaks at 17-18 kDa mass range were also increased in premalignant cells from AAH lesions.

Three peaks are seen with greater intensity in normal respiratory epithelial cells, compared with malignant cells. Peaks at 47102.99 Da (not shown in table) and 66576.6 Da identified at high mass range profile are significantly higher in normal lung epithelial cells, compared with malignant or atypical samples.

Histological Type of Lung Tumors

Squamous Cell Carcinoma

Comparison of protein profile from normal ciliated bronchial and alveolar epithelial cells with profiles from squamous carcinoma (case 3523) show reproducibly increased peaks at 12-23 kDa (FIG. 4) for malignant cells, but not for normal cell samples (Table 1).

Adenocarinoma

Protein profile from adenocarcinoma (case 3322) show increased peaks in the 11-23 kDa mass range. The peak at 17250 Da appeared to be present not only in tumor cells (P=0.001), but also in AAH cells. This peak was not detected in normal alveolar epithelialsepithelial cells (FIG. 5a).

Bronchioloalveolar Carcinoma

Protein spectra of LCM cells from bronchioloalveolar carcinoma (case 3414) show increased peaks in the 17-23 kDa mass range compared with normal alveolar epithelial cells (FIGS. 6a-8b).

Histological appearance of case 3342 showed adenocarcinoma with three foci of bronchioloalveolar, papillary, and focal clear cell features, with significant areas of AAH. SELDI mass spectrometry data for this case identified four distinguishable peaks in the mass range between 7 and 8 kDa (7522.8, 7649.9, 7684.4 and 7948.1 Da). These peaks were not expressed in normal epithelial cells from the same case, yet were not prominent in other study cases. AAH cells from this case showed a peak at 14000 Da with an intensity of 8.90 (P=0.001), which is several fold greater than expression of other protein peaks in atypical cells from this case. Peaks at about 14000 Da also were highly expressed in AAH cells from two other cases (adenocarcinoma, WD and BAC).

Protein mass spectra of Reactive Type II pneumocytes LCM from normal lung tissue adjacent to bronchioloalveolar carcinoma (case 3414) show slight (P=0.054) elevated peaks in 17-23 kDa mass range, but not in normal (non-reactive) alveolar cells. The signal/noise for a possible peak at 14250 Da in both Reactive Type II cell samples was 1.5. Normal cells show small differences in protein expression in the higher mass range (FIG. 6b).

The two sided Mann-Whitney test and Wilcoxon Signed Ranks Test determined that the peaks at 17250 and 17930 were significantly elevated in malignant cells compared with normal cells. The peak at 17250 Da also was detected at low levels in bronchial atypical squamous metaplasia lesion (FIG. 6b, lane 2, A1, from top) and at higher levels in alveolar AAH (lanes 3, 4, A2). The peaks at 17250 Da, showed signal/noise of 2.0 and 3.7 representing bronchial atypia and AAH, respectively (lanes 2 and 4, FIG. 6b). The peak at about 17250 Da shows a several-fold increase compared with undetectable expression in normal lung epithelial cells. The peak at 14000 Da is also significantly increased in cells from AAH compared with normal respiratory epithelial cells.

The proteomic approach to the identification of lung cancer biomarkers can be focused on analysis of proteins of subcellular compartments such as surface membranes, nuclear and cytoplasm proteins. Databases of lung cancer proteins identified by 2-D gel now are available. Multi-dimensional liquid chromatography is another separation mode for lung cancer proteins. The use of protein microarrays for detecting lung cancer antigens or antibodies in sera, biological fluids or cell and tissue lysates potentially contribute to early lung cancer detection.

The proteomic approach disclosed in this invention is based on the analysis of cell-type specific protein expression in malignant lesions detected by helical CT, and in cells exhibiting intermediate morphology associated with neoplastic transformation or differential changes in the airways epithelium. The invention advances the art by providing a method to identify specific protein peaks that show a marked change in expression associated with malignant tumors. The patterns of increases and decreases in protein levels were observed when protein profiles of tumor cells were compared with normal cells. Several peaks showed marked increases in tumor when compared with normal cells. They were at 17250, 17930 and 22250 Da. The peak at 17250 Da was detected in all tumor cell types studied. This peak at 17250 Da was not detected in any of the normal cell LCM's (with a limit of detection of about 5% of tumor levels, P<0.001) and appeared to be present at low levels in AAH samples.

Two other peaks from atypia (AAH) samples show intensities of protein expression, which fall between the intensities for normal and tumor samples peaks at 14000 and 17296.8 Da (Table 1). Cells from peripheral atypical adenomatous (AAH) lesions intensively express proteins at low mass range, such as 7522.8, 7649.9, 7684.4, and 7948.1 Da. These last four protein peaks in combination with three other peaks detected in AAH cells at 14-18 kDa mass range (14000.0, 17250.0 and 17926.8 Da) form a specific protein signature for premalignant AAH lesions of the lung.

High mass range profile peaks (47102.9 and 66576.6 Da) were found at significantly greater intensities in normal lung epithelial cells, compared with malignant or atypical samples. This represents decreasing expression, or possible breakdown of these proteins to shorter peptides during malignant change in peripheral lung epithelium.

In FIG. 10, the evolution of normal cells (20) to premalignant cells (30) to cancerous cells (40) is represented. The invention, denoted as (10), includes the steps of identifying tissue from asymptomatic individuals (52), gathering a substantially homogenous cell population (62) from the tissue by laser capture microdissection (LCM), analyzing the population with mass spectrometry to obtain a peptide profile (72) and identifying predetermined peaks or biomarkers (80) in the mass spectrometry associated with an overexpression of proteins (90) in premalignant cells. The mass spectrometry is done by time-of-flight apparatus, and preferably a SELDI ProteinChip® mass reader available from Ciphergen Biosystems, Fremont, Calif. Asymptomatic tissue may be identified by helical computed tomography. The tissue is retrieved and cryopreserved before sectioning. The LCM may be performed with an appropriate LCM apparatus including an AutoPix™ Automated Laser Capture Microdissection System or PixCell® IIe Laser Capture Microdissection System from Arcturus Engineering, Mountain View, Calif. Predetermined peaks discovered in the present invention include those at approximately 12348, 13794, 14010, 17250, 1726.8, 17922, 17930, 22250 and 22810 Da which constitute biomarkers (100) for premalignant lung cells.

Figure 11:
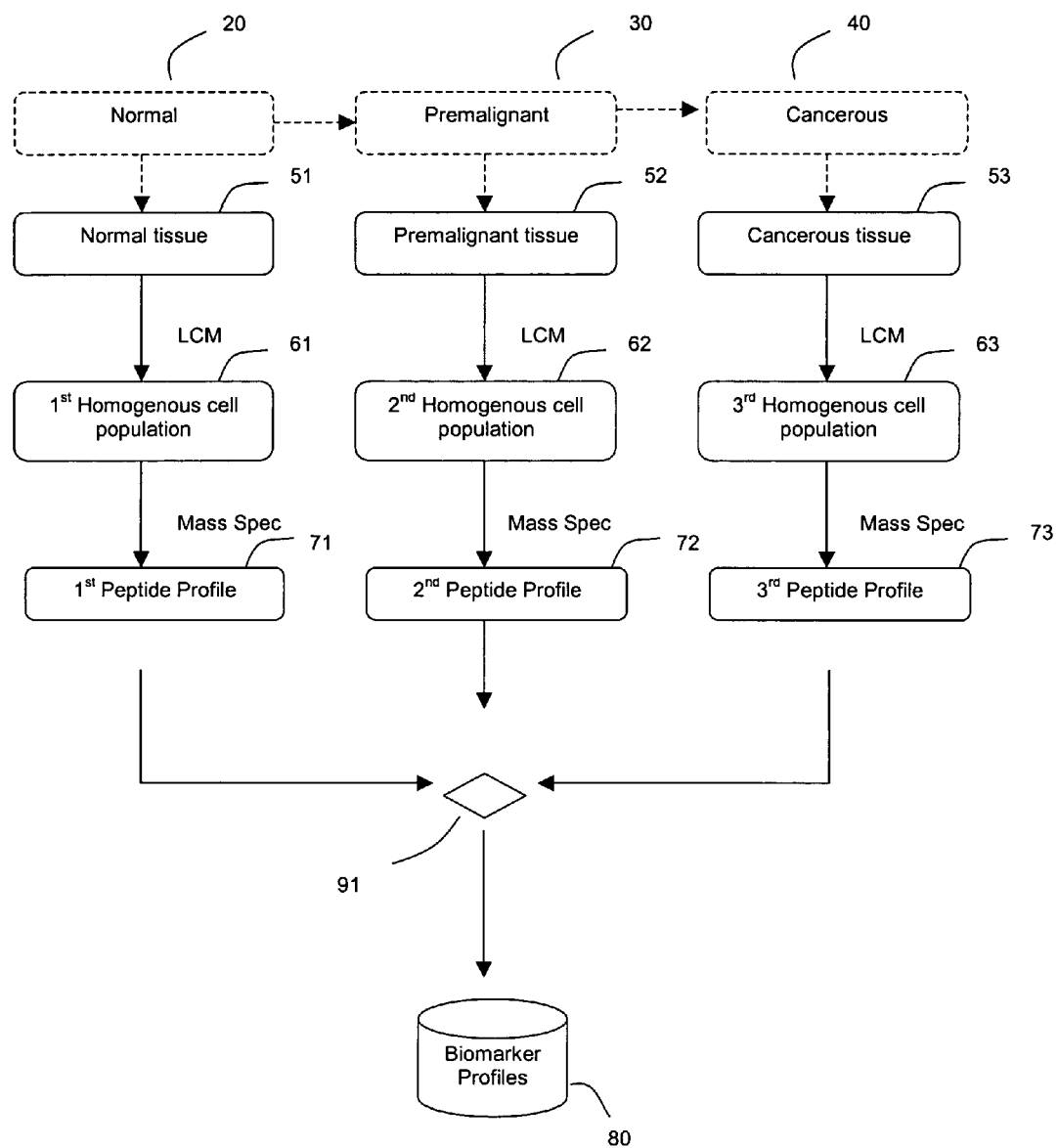
FIG. 11 is a diagrammatic view of an alternative embodiment of the invention for resolving new biomarkers.

FIG. 11 shows a method for identifying premalignant cell biomarkers including the steps of identifying tissue known to be normal (51), identifying tissue known to be premalignant (52), and identifying tissue known to be malignant (53). A first substantially homogenous cell population is gathered (61) from the normal tissue (51) by laser capture microdissection. A second substantially homogenous cell population is gathered (62) from the premalignant tissue (52) by laser capture microdissection. A third substantially homogenous cell population is gathered (63) from the malignant tissue (53) by laser capture microdissection. Each resulting peptide profile (71-73) is then comparatively analyzed by differentiating the peaks (91) in the mass spectrometry to discern new biomarkers (80).

Figure 12:
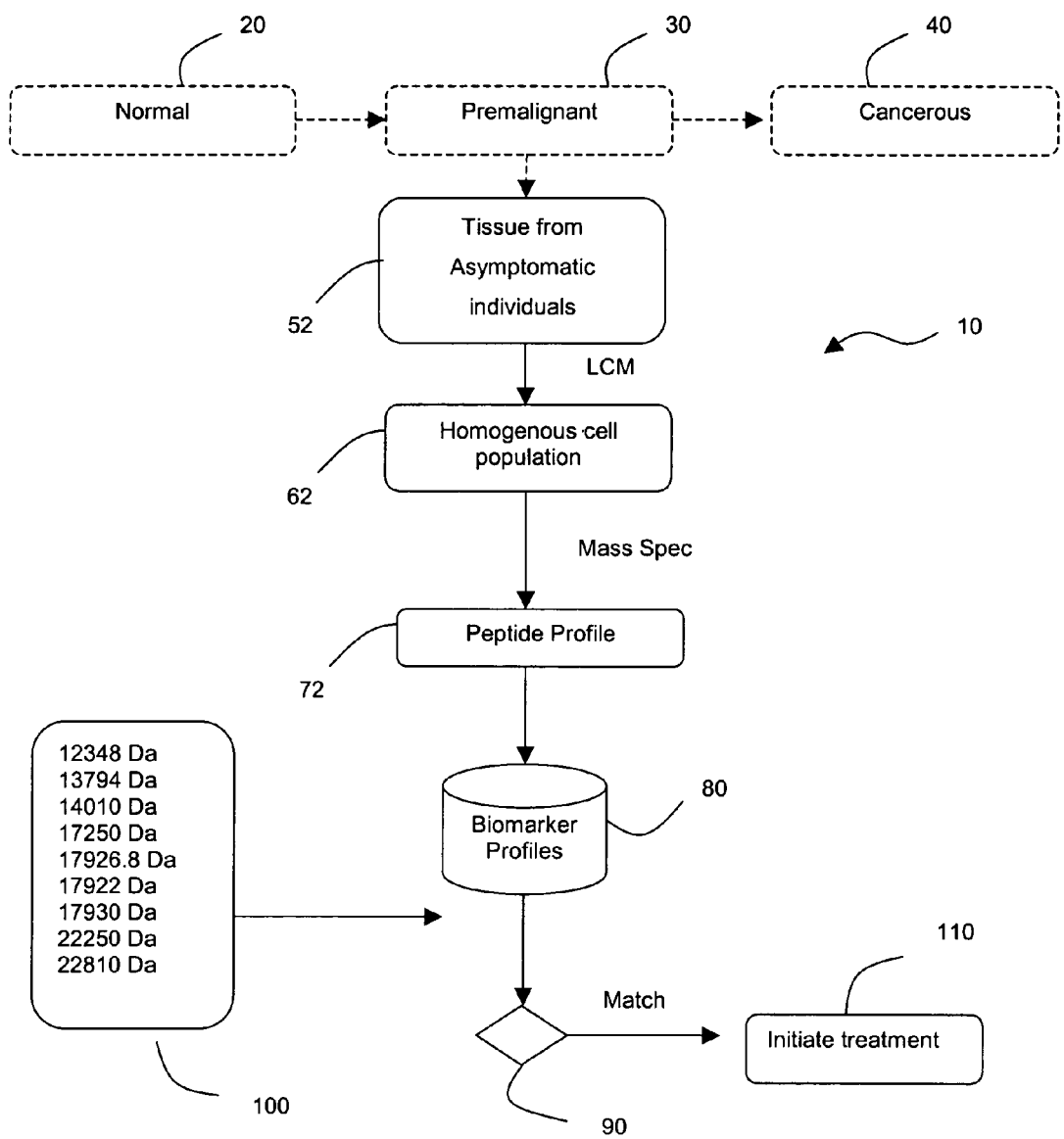
FIG. 12 is a diagrammatic view of an alternative embodiment of the invention for detecting and treating patients with premalignant cells.

FIG. 12 shows an alternative embodiment of the invention including the steps of identifying tissue from asymptomatic individuals (52), gathering a substantially homogenous cell population (62) from the tissue by laser capture microdissection (LCM), analyzing the population with mass spectrometry to obtain a peptide profile (72), identifying predetermined peaks or biomarkers (80) in the mass spectrometry associated with an overexpression of proteins (90) in premalignant cells and initiating a treatment (110) such as administering chemopreventive agents to a patient to prevent or minimize potential malignant growth.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

The invention claimed is:

1. A method for detection of overexpression of proteins in premalignant and malignant cells by identifying at least one predetermined peak in the premalignant and malignant cells, the method comprising the steps of:
gathering a substantially homogenous cell population from lung tissue of asymptomatic individuals to be screened for lung cancer;
analyzing the cell population with SELDI mass spectrometry; and
identifying the at least one predetermined peak in the mass spectrometry associated with the overexpression of proteins in the premalignant and malignant cells, the at least one predetermined peak having an approximate value selected from the group consisting of 12348, 13794, 14010, 15208.7, 15910.5, 17250, 17926.8, 17922, 17930, 22250, 22810, 47102.9 and 66576.6 Da in the mass spectrometry.

2. A method for detection of overexpression of proteins in premalignant and malignant cells by identifying at least one predetermined peak in the premalignant and malignant cells, the method comprising the steps of
detecting lung tissue from asymptomatic individuals to be screened for lung cancer by helical computed tomography;
cryopreserving the tissue;
sectioning the tissue;
gathering a substantially homogenous cell population from the sectioned tissue;
analyzing the cell population with SELDI mass spectrometry; and
identifying the at least one predetermined peak having an approximate value selected from the group consisting of 12348, 13794, 14010, 17250, 17926.8, 17922, 17930, 22250 and 22810 Da in the mass spectrometry associated with the overexpression of proteins in the premalignant and malignant lung cells.

3. A method for detection of under-expression of proteins in premalignant and malignant cells by identifying at least one predetermined peak in the premalignant and malignant cells, the method comprising the steps of:

gathering a substantially homogenous cell population from lung tissue of asymptomatic individuals to be screened for lung cancer;

analyzing the cell population with SELDI mass spectrometry; and identifying the at least one predetermined peak in the mass spectrometry associated with the under-expression of proteins in the premalignant and malignant cells wherein the at least one predetermined peak has an approximate value selected from the group consisting of 15208.7, 15910.5, 47102.9 and 66576.6 Da.

4. A method for detection of under-expression of proteins in premalignant and malignant cells by identifying at least one predetermined peak in the premalignant and malignant cells, the method comprising the steps detecting lung tissue from asymptomatic individuals to be screened for lung cancer by helical computed tomography;

cryopreserving the tissue;

sectioning the tissue;

gathering a substantially homogenous cell population from the sectioned tissue;

analyzing the cell population with SELDI mass spectrometry; and identifying the at least one predetermined peak in the mass spectrometry associated with the under-expression of proteins in the premalignant and malignant cells wherein the at least one predetermined peak has an approximate value selected from the group consisting of 15208.7, 15910.5, 47102.9 and 66576.6 Da.

5. The method according to claim 1 wherein the substantially homogenous cell population is gathered by laser capture microdissection.

6. The method according to claim 2 wherein the substantially homogenous cell population is gathered by laser capture microdissection.

7. The method according to claim 3 wherein the substantially homogenous cell population is gathered by laser capture microdissection.

8. The method according to claim 4 wherein the substantially homogenous cell population is gathered by laser capture microdissection.

* * * * *